United States Patent
Ibragimov

(10) Patent No.: US 8,366,649 B2
(45) Date of Patent: Feb. 5, 2013

(54) MANUALLY OPERATED DISPOSABLE SINGLE-NEEDLE CIRCUIT FOR EXTRACORPOREAL TREATMENT OF BLOOD

(76) Inventor: Araz Ibragimov, Brooklyn, NY (US)

( * ) Notice: Subject to any disclaimer, the term of this patent is extended or adjusted under 35 U.S.C. 154(b) by 541 days.

(21) Appl. No.: 12/634,121

(22) Filed: Dec. 9, 2009

(65) Prior Publication Data
US 2011/0137224 A1    Jun. 9, 2011

(51) Int. Cl.
*A61M 37/00* (2006.01)
(52) U.S. Cl. .......... 604/6.1; 604/4.01; 604/6.09
(58) Field of Classification Search ......... 604/4.01–6.16
See application file for complete search history.

(56) References Cited

U.S. PATENT DOCUMENTS

| | | | |
|---|---|---|---|
| 4,599,093 A | 7/1986 | Steg | |
| 4,614,590 A * | 9/1986 | Rath et al. | 210/637 |
| 4,842,576 A | 6/1989 | Lysaght | |
| 5,298,020 A * | 3/1994 | Stone | 604/6.05 |
| 5,330,425 A | 7/1994 | Utterberg | |
| 5,776,091 A * | 7/1998 | Brugger et al. | 604/6.1 |
| 6,059,745 A | 5/2000 | Gelbfish | |
| 6,284,131 B1 * | 9/2001 | Hogard et al. | 210/143 |
| 7,381,195 B2 * | 6/2008 | Mori et al. | 604/6.08 |
| 7,540,958 B2 * | 6/2009 | Chevallet et al. | 210/258 |

* cited by examiner

*Primary Examiner* — Philip R Wiest
(74) *Attorney, Agent, or Firm* — Boris Leschinsky

(57) ABSTRACT

A disposable single-needle extracorporeal blood treatment circuit for such treatments of blood hemofiltration, plasma filtration, detoxification and alike includes a manually operated syringe attached to a proximal bifurcation and a patient's access port attached to a distal bifurcation. Both bifurcations are connected with each other by a withdrawal line and in parallel by a treatment loop including a blood treatment unit and an air removal element. In the first embodiment, one or two three-way valves (such as stop-cocks) are positioned at these bifurcations to allow directing the flow of blood from the patient to the syringe through the withdrawal line and redirecting the flow through the treatment loop when blood is being returned to the patient from the syringe. In a second embodiment, two check valves are positioned along said withdrawal line and said treatment loop to automatically direct the blood floe in the same manner. Additional flush and drain circuits are optionally included allowing a "stand-by" mode of operation.

14 Claims, 6 Drawing Sheets

MANUALLY OPERATED DISPOSABLE SINGLE-NEEDLE CIRCUIT FOR EXTRACORPOREAL TREATMENT OF BLOOD

BACKGROUND OF THE INVENTION

The present invention relates to extracorporeal blood treatment circuits, more specifically to a manually operated single-needle apparatus for treating blood, in particular aimed at removing toxins and metabolic products therefrom.

Unlike continuous circulating of blood through a treatment element in the same direction in which the patient's skin and vessels have to be punctured with two separate needles for taking the blood from his or her body and running it back thereto, single-needle blood treatment circuits uses only one needle. Such blood treatment offers the useful effect that the number of punctures is decreased from two to one so that, on the one hand, there is less damage to the vessels while on the other hand pain produced when puncturing the skin is reduced.

Historically, kidney disease has been of critical concern to human life. Many kinds of kidney diseases interfere with the function of the kidney such that the kidney ceases to remove waste and excess water from the blood. When the kidney is sufficiently impaired that a large portion of the waste products and water are not removed from the blood, the life of the patient cannot be preserved unless a way is provided for artificially performing the function of the impaired kidney. Many new developments have come to light, which perform the function of the impaired kidney extracorporeally. Nevertheless, even with the existing improvements in extracorporeal kidney apparatus, the same general procedure is used for processing patients' blood that was used very early in the treatment of kidney disease.

For example, the most commonly accepted practice for treating a patient's blood extracorporeally requires the surgical creation of a subcutaneous, arterio-venous fistula. Thereafter, the subcutaneous venous system dilates secondary to the increase of blood flow derived from the artery to the vein through the fistula. Sufficient blood flow for blood treatment extracorporeally is then obtainable by venipuncture with large bore needles. Normally, two hollow needles or cannulas are used to perform two venipunctures on the patient so that two blood-communication sites exist simultaneously in the patient. Conventionally, blood is withdrawn from one of the punctured blood vessels, forced through a blood treatment circuit and thereafter forced into the other by the use of an extracorporeal pump, typically a peristaltic pump controlled by a sophisticated drive system equipped with a number of pressure sensors.

The aforementioned procedure has been found to have serious disadvantages both to the patient and to the attending physicians and technicians. The problems are particularly aggravated because most patients requiring extracorporeal blood treatment must undergo this treatment as frequently as three to seven times per week. This means that if every venipuncture were completely successful, a patient would need to undergo from 6 to 14 venipunctures or cannulations each week. Besides, in case of an emergency or in the field where this equipment is not available, it is practically impossible to initiate such treatment on a short notice.

It is well known that the duration and proper function of a fistula created by venipuncture is inversely related to the number of venipunctures. Tissue repeatedly subjected to the trauma of venipuncture is much more susceptible to thrombophlebitis, paravascular hemorrhage, clotting and infection. In fact, it is commonly found in patients who have experienced a number of venipunctures, that the tissues surrounding the most accessible veins develop large hematomas which obscure the veins making successful venipuncture extremely difficult because of insufficient blood flow in the damaged blood vessels.

Also contributing to the problem is the fact that once one successful venipuncture is made and blood is allowed to flow from the patient's body toward an extracorporeal blood treatment circuit, the blood volume in the patient's body is reduced making the second venipuncture very difficult. Historically, it has been found that while most skilled physicians or technicians are able to perform the first venipuncture with little difficulty, frequently a plurality of attempts is necessary before a second venipuncture can be performed on the same patient.

To address a number of concerns enumerated above, a single-needle blood treatment circuit was invented. Single-needle systems are known in the art and basically operate by cyclically withdrawing a volume of blood from a patient, passing it through a blood treatment unit, and returning it to the patient. The process then repeats, intermittently processing volumes of blood through the blood treatment unit. A single needle is used for both withdrawing and returning the blood—hence the name. It accomplishes the same result using only one puncture of the vein.

To provide a comprehensive disclosure without unduly lengthening this specification, applicant incorporates by reference in their entireties the disclosures of U.S. Pat. Nos. 3,756,234, 3,830,234, 3,848,592, 3,938,909, 4,063,554, 3,908,653, 3,756,234, 3,811,800, 3,830,234, 3,985,134, 4,490,134, 4,614,590, 4,776,837, 5,358,482, 5,871,459, and 6,074,359 which show various single needle blood treatment devices and teach certain fundamental concepts useful in the construction of a device according to the present invention. They all basically describe a circuit having a single-needle access to the patient's blood system equipped on the back end with a bifurcation to separate the blood flow into two lines. A blood flow loop is then formed starting from one line of the bifurcation and ending with another. A pump and blood treatment apparatus are located along this loop as well as various other devices such as valves, filters, etc.

With all the systems of the prior art however, a complicated piece of equipment is still required to perform a single-needle dialysis. In addition, highly skilled personnel are needed to operate such equipment. Besides, due to dilution or drawing of blood out of the patient during the priming of the circuit, this approach may not be used with neonates or such patients who are sensitive to reduction of blood volume. The need exists to address these limitations of the present day single-needle blood treatment devices.

The situation of acute toxicity for a large number of patients located in the field or another remote site such as for example during war or mass casualties in a terrorist attack presents a special challenge for medical personnel. With the devices available at present time, there is no practical way to initiate the acute extracorporeal blood treatment needed for many people at once in such circumstances. The need exists therefore for an extracorporeal detoxification circuit allowing for blood treatment without the need for electrical power, complicated equipment and highly trained personnel.

SUMMARY OF THE INVENTION

Accordingly, it is an object of the present invention to overcome these and other drawbacks of the prior art by providing a novel manually operated disposable extracorporeal circuit for treating blood via a single-needle puncture.

It is another object of the present invention to provide a circuit for treating blood without the use of electrical power, especially advantageous in the field conditions.

It is a further object of the invention to provide a disposable low-cost self-contained extracorporeal circuit for treating blood operable without the use of any power driven medical equipment.

It is a further object of the present invention to provide a disposable extracorporeal circuit for treating blood requiring only minimal user training and low level medical skills to operate thereof.

It is yet a further object of the present invention to provide a disposable extracorporeal circuit for treating blood with minimal priming volume so that such treatment can be administered to pediatric patients including neonates as well as patients sensitive to blood dilution or temporary reduction in blood volume.

It is yet another object of the present invention to provide an extracorporeal circuit for treating blood capable of intermittent operation with active periods and passive "stand-by" periods without the risk of clotting the circuit during the "stand-by" periods.

The present invention, including a novel disposable blood treating circuit, reduces patient trauma and tissue damage by accommodating extracorporeal blood treatment or detoxification with a single venipuncture. Generally, once the venipuncture has been performed, blood is pulled away from the venipuncture site through a blood withdrawal path. The blood is forced back into the patient through a blood treatment path. Two three-way valves or check valves are used to switch blood pathway from withdrawal to treatment and return as described in greater detail below.

The operation of the circuit using the single venipuncture is made possible by alternating the blood flow into and out of the patient at the venipuncture site. A unidirectional blood flow through the blood treatment unit of the circuit is established by alternating a push and pull operation of the syringe and changing the position of two three-way valves to periodically connect the syringe cavity either to the blood withdrawal path or blood treatment path.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE FIRST MOST PREFERRED EMBODIMENT OF THE INVENTION

A detailed description of the first and most preferred embodiment of the present invention follows with reference to accompanying drawings in which like elements are indicated by like reference letters and numerals.

Figure 1:
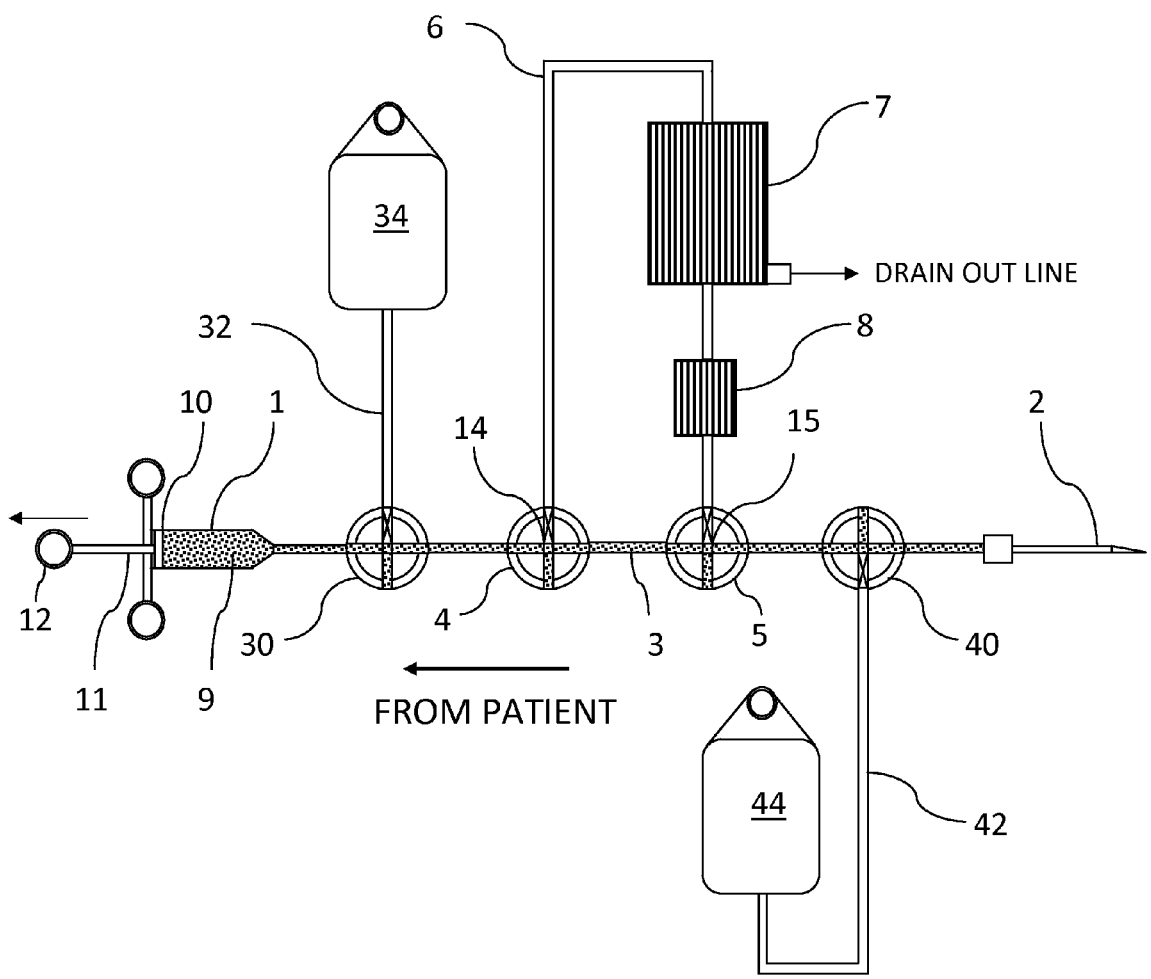
FIG. 1 is a block-diagram of the first embodiment of the novel circuit of the present invention containing two main manually operated three-way valves, shown is a state of blood withdrawal.

FIG. 1 shows a general block-diagram of the circuit to include a manually operated volume displacement pump 1 (such as a syringe) connected to a single-needle access port 2 of the patient through a distal circuit bifurcation 15 (defined as the closest to the patient) and a proximal circuit bifurcation 14 (defined as the closest to the pump). Line 3 between the distal 15 and proximal 14 bifurcations defines a blood withdrawal path. The blood withdrawal path is shown with dotted fill in FIG. 1 and includes two three-way valves: a first three-way valve 5 located at the distal bifurcation 15 and a second three-way valve 4 located at the proximal bifurcation 14. Valves 4 and 5 are typically simple Luer stop-cock valves commonly used in blood handling circuits.

Besides line 3, three-way valves 4 and 5 located at the respective proximal 14 and distal 15 bifurcations define a closed loop line 6 forming a blood treatment path. It includes a blood treatment unit 7 and optionally an air removal element 8.

Additional optional elements of the circuit of the present invention include a flush portion starting from the flush bag 34 connected to the circuit through the flush line 32 and a three-way flush valve 30. A drain portion of the circuit comprises a three-way drain valve 40 to connect the drain reservoir 44 through the drain line 42.

Figure 2:
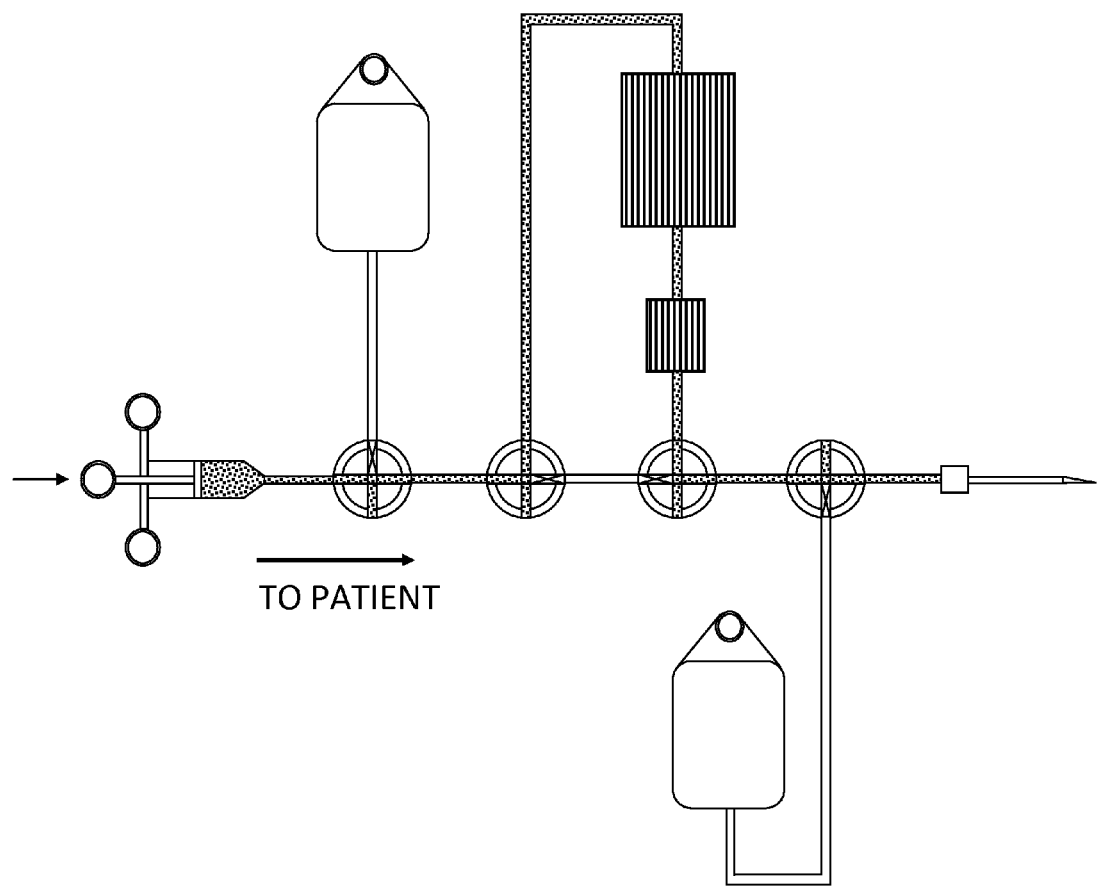
FIG. 2 is the same circuit as in FIG. 1 when the three-way valves are switched for blood treatment and return to the patient.

Typically, the three-way valves 4 and 5 have two positions: the first position is the "BLOOD WITHDRAWAL" position as shown in FIG. 1. In this position, the valves are turned to connect the pump 1 to the access port 2 via line 3 while the blood treatment loop 6 is completely isolated from the blood flow path. A second position is a "TREATMENT AND RETURN" position when the valves 4 and 5 are turned to connect the blood treatment loop 6 into the blood pathway and exclude the line 3 therefrom as shown in FIG. 2. Initially, such as in storage position, the three-way valves 4 and 5 may be placed in "ALL CLOSED" position preventing flow in all directions. High-bore three-way stop-cock valves are preferred to be used as valves 4 or 5 since they allow a comparatively high blood flow to be drawn therethrough.

Various commonly known blood filters can be used as a blood treatment unit 7 to include as examples the following: a hemofilter, a mass-exchange device, a plasma filter for plasmapheresis, a hemoconcentrator, a hemoperfusion column equipped with charcoal for separation of toxic elements from blood, a UV-irradiation device for deactivating of blood-born bacteria and similar organisms, etc. Some of these elements may require a drain-out line shown in FIG. 1. It is important to select this element to have the lowest available priming volume to minimize the priming volume of the entire circuit. With some of the blood treating devices available on the market today, it is estimated that the minimum priming volume of the entire circuit of the invention may be as low as only 5-10 cc.

An air removal element 8 is needed for initial priming of the device and to ensure an air-free return flow of blood during the treatment period. A bubble-trap or a drip chamber may be advantageously used as an air removal element 8. Both of these devices can effectively remove air without the use of electrical power and therefore suit the purpose of the present invention advantageously. Again, it is important to keep the priming volume of this element down so that the overall priming volume of the circuit is minimized. An optional blood filter may also be included in the circuit (not shown) to eliminate any foreign particles from being passed onto the patient.

A volume displacement pump 1 of the invention is most preferably a manually operated syringe having a blood cavity 9, a piston 10 activated by hand via a rod 11, which is optionally equipped with finger ring 12. The piston 10 is preferably positioned all the way into the cavity 10 for the storage of the circuit to facilitate the smaller size of the storage package as well the immediate activation of the circuit since aspiration is envisioned to be the first action of the pump.

In use, venous or arterial access is obtained using the commonly known techniques. The access port 2 is established and attached to the circuit, which may contain a quick-connect coupling adapted for this purpose (not shown). The valves 4 and 5 are turned to "BLOOD WITHDRAWAL" position to open line 3 and isolate line 6. The circuit may be first primed with any common blood compatible solution such as saline or primed with patient's own blood as will be described in more detail below.

The physician or another qualified user of the device then pulls on the piston 10 of the pump 1 via a rod 11 using the finger ring 12. Blood is evacuated into the cavity 9 through both valves 4 and 5 and line 3. To treat and return blood back into the access port 2, the user turns the valves 4 and 5 to the "TREATMENT AND RETURN" position to isolate line 3 and connect loop 6 into the circuit as shown in FIG. 2. When three-way stop-cocks are used, the valve 4 is turned 90 degrees clockwise, while the valve 5 is turned 90 degrees counterclockwise. Pushing on the rod 11, the user then applies pressure to the blood and forces it out of the cavity 9 through the valve 4 into the loop 6 and into the blood treatment unit 7. The treated blood comes out of the unit 7, passes through the air removal element 8, valve 5 and back into the access port 2 to be returned to the bloodstream of the patient.

The valves 4 and 5 are returned then back to the "BLOOD WITHDRAWAL" position so that the same action can be repeated.

In a useful variation of the circuit according to the first embodiment of the invention, only one three-way valve 4 at the proximal bifurcation 14 can be used and the other bifurcation may contain all three lines connected together. This configuration is not shown on the drawings but would be readily understood by those skilled in the art. All that is needed for a successful operation of the circuit in that case is the blood treating unit 7 and the air removal element 8 to have hard-shell housings to prevent their collapse during blood withdrawal stage of the procedure. The advantage of this configuration is the ease of use of the circuit since only one valve has to be operated by the user.

DETAILED DESCRIPTION OF THE SECOND PREFERRED EMBODIMENT OF THE INVENTION

Figure 3:
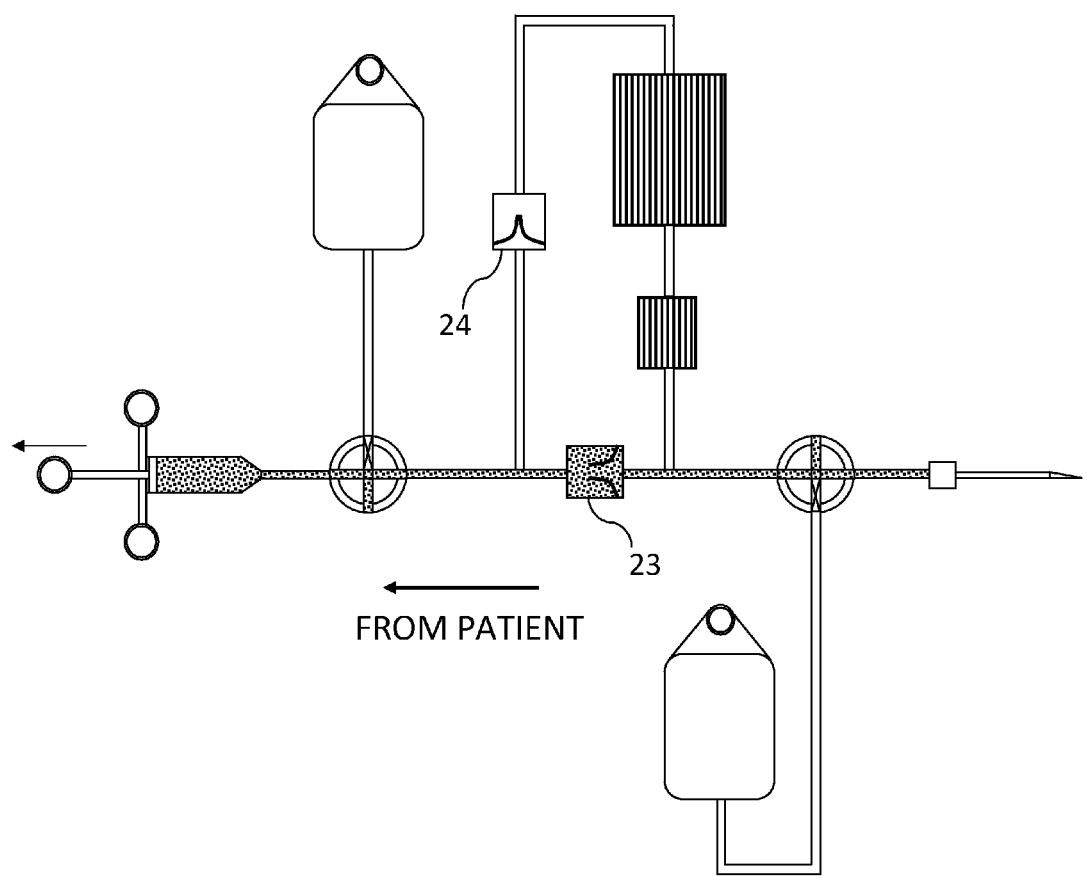
FIG. 3 is a block-diagram of the second embodiment of the invention showing the blood treating circuit equipped with two check valves, shown is the state of blood withdrawal.
Figure 4:
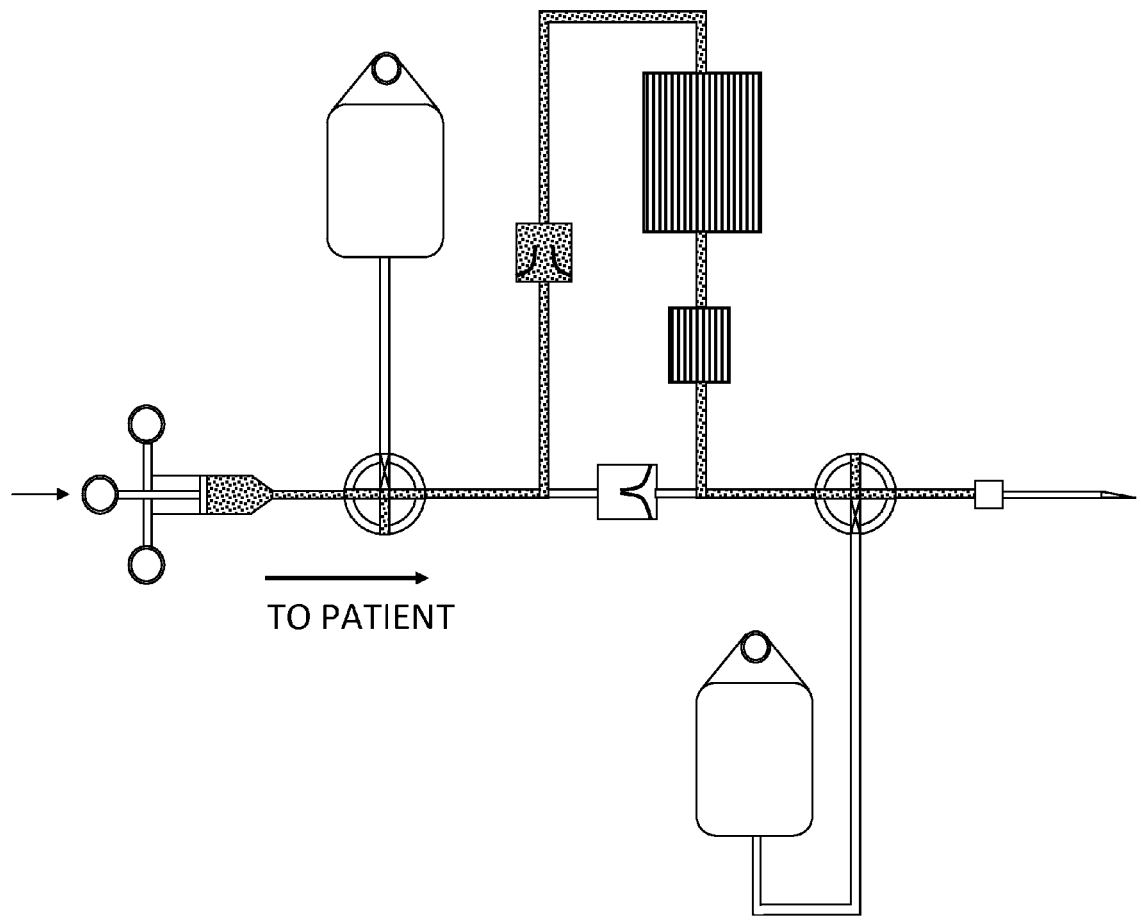
FIG. 4 is the same circuit as in FIG. 3 but in a state of blood treatment and return to the patient.

A detailed description of the second preferred embodiment of the present invention follows with reference to accompanying drawings in FIGS. 3 and 4. The circuit includes all the same main elements as in the first embodiment of the invention. Specifically, the manual pump 10 (such as a syringe) is connected with the proximal bifurcation 14 of the circuit and the access port 2 is connected with the distal bifurcation 15 of the circuit. Two bifurcations 14 and 15 are connected with each other by both the "BLOOD WITHDRAWAL" line 3 and the "TREATMENT AND RETURN" loop 6. The loop 6 includes a serially connected blood treatment unit 7 followed by an air removal element 8. These elements are similar in design to that described above for the first embodiment of the invention.

The main difference is the presence of two check valves. The "BLOOD WITHDRAWAL" check valve 23 is located between both bifurcations 14 and 15 along the line 3 and oriented to allow flow from distal bifurcation 15 towards the proximal bifurcation 14 but not in the opposite direction. The "TREATMENT AND RETURN" check valve 24 is located also between the bifurcations 14 and 15 but in the loop 6 and allows flow to go from the proximal bifurcation 14 along the treatment loop 6 and towards the patient. Its most preferred location is between the proximal bifurcation 14 and the blood treatment unit 7 although it is possible to position it after the unit 7 and also after the element 8 but before the distal bifurcation 15.

Various known designs of check valves can be used in the circuit of the invention. They include duckbill valve, ball valve, flapper valve, etc. A duckbill or ball valves are preferred for the circuit of the invention because they allow for easy priming of the circuit.

The advantage of the circuit of the second embodiment is the automatic function of the device during both the withdrawal and return stages of the treatment without the need to manually operate the valves. As the user pulls on the manual pump 1, blood is drawn from the patient into the circuit and along line 3 while loop 6 remains closed. Upon reversal of the pump operation, when pressure is developed inside the pump, blood is forced through the loop 6 to be treated and returned back to the patient.

The present invention has several particular advantages as outlined above in detail and therefore can be advantageously used in the following blood treatment circumstances:

- as a plasma filtration unit for acute crash syndrome;
- for urgent extracorporeal hemofiltration in cases of diuretic-resistant acute lung edema;
- for extracorporeal detoxification of neonates and newborn babies;
- for extracorporeal detoxification and/or plasma filtration in the field, in situations of power failure, in a war zone, for mass casualties and terrorism attacks, triage areas of mass disasters, etc.

DETAILED DESCRIPTION OF ADDITIONAL ELEMENTS OF THE CIRCUIT

FIG. 1 further shows additional optional elements of the circuit that can be used with both the first or a second embodiment of the invention, these elements are now described in greater detail.

Figure 5:
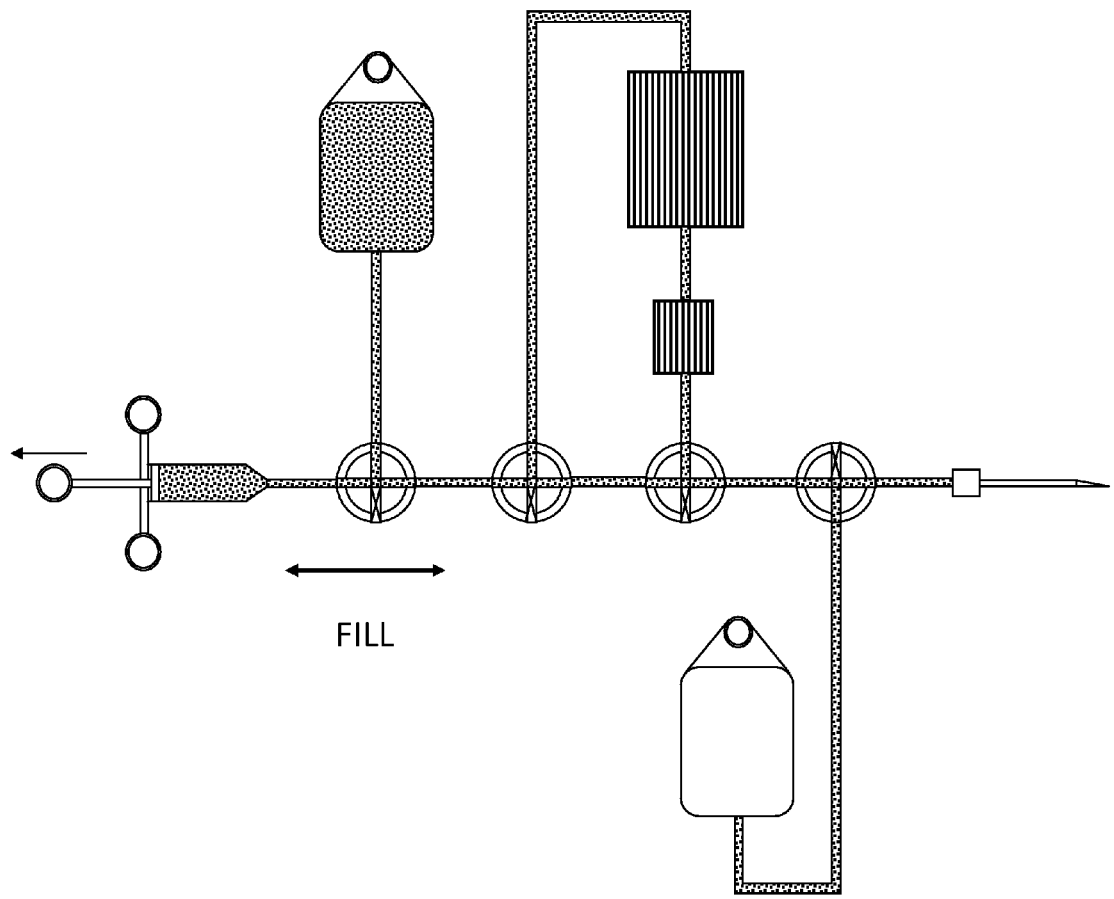
FIG. 5 shows a state of the circuit from FIG. 1 adapted for initial fill with the priming fluid, and finally

Flush circuit may be optionally included in the circuit by adding a flush three-way valve 30 connected with a source of priming and flushing fluid such as a reservoir 34 via a line 32. This circuit may be activated during the initial priming of the entire circuit of the invention by selecting the appropriate position of the valve 30. FIG. 5 shows the valve in a position allowing retrieval of the priming fluid from the reservoir 34. The height of the reservoir 34 is used to fill the entire system of the invention.

Figure 6:
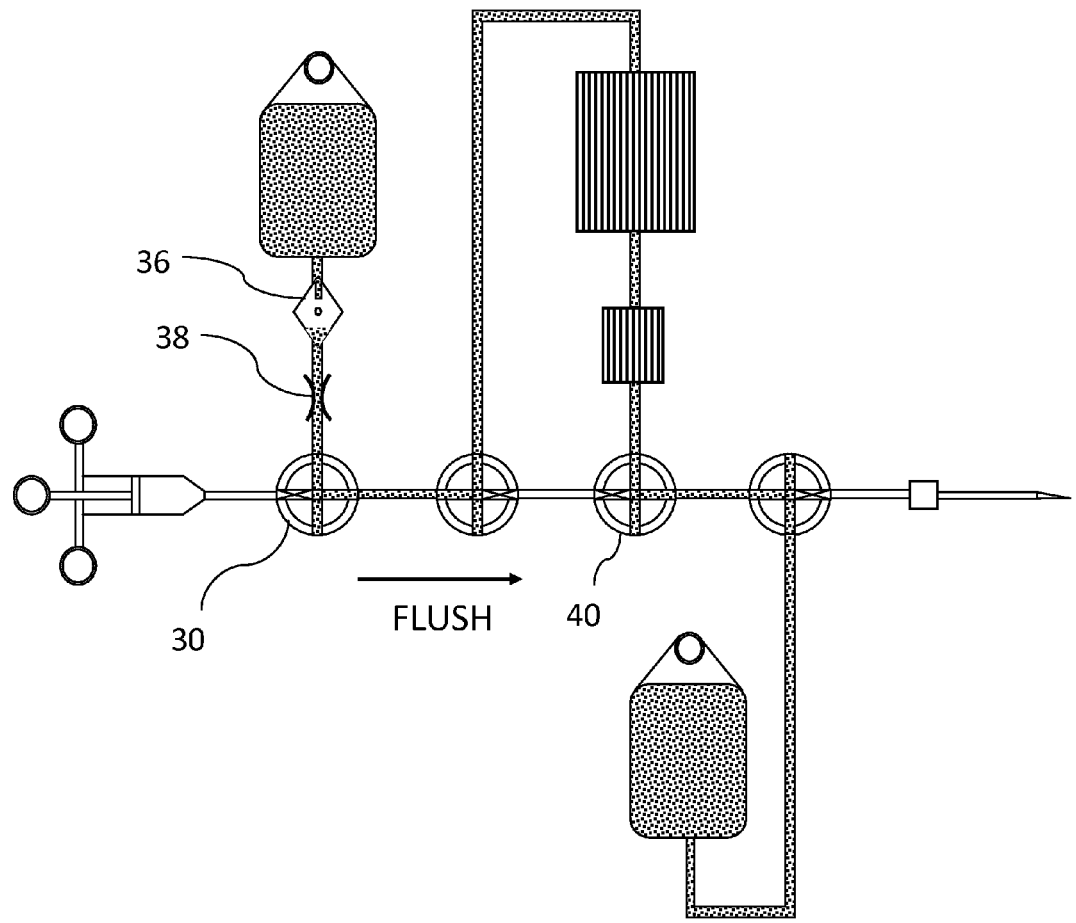
FIG. 6 shows a state of the circuit from FIG. 1 adapted for temporary holding the treatment and provide flush to the circuit so as to avoid clotting.

Additionally, drain circuit is optionally provided including a drain three-way valve 40 connected to a drain reservoir 44 through a line 42. Flush and drain circuits are connected to the main circuit of the invention during "stand-by" passive periods when the treatment of blood is not needed but may be required again. In this case, the blood is first flushed from the circuit back into the patient and then the valves 30 and 40 are placed in the "FLUSH" state shown in FIG. 6 to initiate a slow flush of the circuit in order to avoid forming clots inside thereof. The flush portion of the circuit may include additional elements allowing for slow flush such as a drip chamber 36 and an adjustable restrictor 38 shown in FIG. 6.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A manually operated single-needle circuit for extracorporeal treatment of blood comprising:
   a displacement pump configured to be manually operated to cause blood flow,
   a withdrawal line,
   a treatment loop including a blood treatment element,
   a proximal bifurcation connected to said pump, said withdrawal line and said treatment loop,
   a distal bifurcation connected to said withdrawal line, said treatment loop and configured to be connected to a single needle for withdrawal and return of blood from a patient, and
   a flow directing means to direct the blood flow through said withdrawal line in a direction from said patient into said pump while isolating said treatment loop during withdrawal of said blood from said patient to said pump, said flow directing means further adapted to direct the blood flow in a direction from said pump to said patient through said treatment loop while isolating said withdrawal line during return of said blood from said pump to said patient.

2. The circuit as in claim 1, wherein said treatment loop further comprising an air removal element.

3. The circuit as in claim 1, wherein said flow directing means comprise a manually operated three-way valve at said distal bifurcation.

4. The circuit as in claim 1, wherein said flow directing means comprise a manually operated three-way valve at said proximal bifurcation.

5. The circuit as in claim 1, wherein said pump is a syringe.

6. The circuit as in claim 1, wherein said flow directing means comprise a first check valve positioned in said withdrawal line and oriented to allow said blood flow only in the direction from said distal bifurcation to said proximal bifurcation, said flow directing means further including a second check valve positioned in said treatment loop and oriented to allow said blood flow only in the direction from said proximal bifurcation to said distal bifurcation.

7. The circuit as in claim 1 further including a flush three-way valve located between said pump and said proximal bifurcation, said flush valve allowing connecting a flush fluid reservoir to said circuit.

8. The circuit as in claim 1 further including a drain three-way valve located between said distal bifurcation and said patient, said drain valve allowing connecting a drain fluid reservoir to said circuit.

9. A manually operated disposable single-needle circuit for extracorporeal treatment of blood comprising:
   a syringe,
   a withdrawal line,
   a treatment loop including a blood treatment unit and an air removal element,
   a proximal bifurcation connected to said syringe, said withdrawal line and said treatment loop, said proximal bifurcation containing a first three-way stop-cock valve,
   a distal bifurcation connected to said withdrawal line, said treatment loop and configured to be connected to a single needle for withdrawal and return of blood from a patient, said distal bifurcation containing a second three-way stop-cock valve,
   wherein said first and said second three-way stop-cocks are adapted to direct the blood flow through said withdrawal line in a direction from said patient into said syringe during blood withdrawal while isolating said treatment loop, said first and said second three-way stop-cocks adapted also to direct the blood flow through said treatment loop in a direction from said syringe to said patient while isolating said withdrawal line during return of said blood to said patient.

10. The circuit as in claim 9, wherein said blood treatment unit is a mass-exchange filter.

11. The circuit as in claim 9, wherein said blood treatment unit is a hemofiltration filter.

12. The circuit as in claim 9, wherein said blood treatment unit is a plasma filtration filter.

13. The circuit as in claim 9, wherein said air removal element is a drip chamber.

14. The circuit as in claim 9, wherein said air removal element is a bubble trap.

* * * * *